United States Patent

Nakamura et al.

Patent Number: 5,374,750
Date of Patent: Dec. 20, 1994

[54] METHOD AND MANUFACTURING OF FATTY ACID ESTERS OF POLYOXYALKYLENE ALKYL ETHERS

[75] Inventors: Hirofumi Nakamura, Narashino; Itsuo Hama, Chiba; Yuji Fujimori, Narashino; Yuichi Nakamoto, Nagareyama, all of Japan

[73] Assignee: Lion Corporation, Tokyo, Japan

[21] Appl. No.: 114,189

[22] Filed: Sep. 1, 1993

Related U.S. Application Data

[63] Continuation of Ser. No. 820,979, Jan. 15, 1992, abandoned.

[30] Foreign Application Priority Data

Jan. 18, 1991 [JP] Japan .................................. 3-16780
Mar. 5, 1991 [JP] Japan .................................. 3-63904

[51] Int. Cl.$^5$ ............................................. C07C 51/00
[52] U.S. Cl. .................................... 554/149; 568/618; 426/417; 426/581; 426/586
[58] Field of Search .......................... 554/149; 568/618; 426/417, 581, 586

[56] References Cited

U.S. PATENT DOCUMENTS 5,012,012   4/1991   Nakamura et al. .................. 568/618

FOREIGN PATENT DOCUMENTS 335295   10/1989   European Pat. Off. ............ 554/149
1164437   of 0000   Japan .
3636431   4/1981   Japan .
5636431   4/1981   Japan .

OTHER PUBLICATIONS

Translation of JP 56-36431 (Aug. 1993).

*Primary Examiner*—José G. Dees
*Assistant Examiner*—Deborah D. Carr
*Attorney, Agent, or Firm*—Bacon & Thomas

[57] ABSTRACT

In a method of manufacturing fatty acid esters of polyoxyalkylene alkyl ethers, fatty acid alkyl ester is reacted with alkylene oxide in the presence of a catalyst consisting essentially of a magnesium oxide added with at least one metal ion selected from the group consisting of $Al^{3+}$, $Ga^{3+}$, $In^{3+}$, $Tl^{3+}$, $Co^{3+}$, $Sc^{3+}$, $La^{3+}$, and $Mn^{2+}$ to manufacture a compound having the following formula:

$$R_1 \overset{O}{\overset{\|}{C}} (OR_2)_n OR_3$$

wherein each of $R_1$ and $R_3$ independently represents an alkyl group, $R_2$ represents an alkylene group, and n is a positive integer.

12 Claims, No Drawings

METHOD AND MANUFACTURING OF FATTY ACID ESTERS OF POLYOXYALKYLENE ALKYL ETHERS

This application is a continuation of application Ser. No. 07/820,979, filed Jan. 15, 1992.

BACKGROUND OF THE INVENTION

1. Field of the Invention

The present invention relates to a method of manufacturing fatty acid esters of polyoxyalkylene alkyl ethers and, more particularly, to a method of manufacturing fatty acid esters of polyoxyalkylene alkyl ethers obtained such that a fatty acid alkyl ester and an alkylene oxide are directly reacted with each other using a magnesium oxide catalyst added with a metal ion.

2. Description of the Related Art

Fatty acid esters of polyoxyalkylene alkyl ethers are known an ether ester-type nonionic surfactant. Of all fatty acid esters of polyoxyalkylene alkyl ethers, polyoxyethylene stearyl ether stearates having the following formula, for example, is used as an emulsion, a dispersant, or an oil-phase adjustor in cosmetics or in a variety of industrial fields:

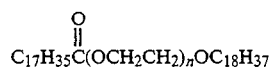

$$C_{17}H_{35}\overset{O}{\overset{\|}{C}}(OCH_2CH_2)_nOC_{18}H_{37}$$

Use of polyoxyethylene methyl ether laurates originated from a lower alkyl ether having the following formula as a wetting agent has been studied (JAOACS, 56:873 (1973)):

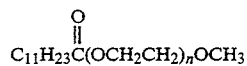

$$C_{11}H_{23}\overset{O}{\overset{\|}{C}}(OCH_2CH_2)_nOCH_3$$

A polyoxyethylene alkyl ether and a polyoxyethylene fatty acid ester as typical ethylene oxide type nonionic surfactants can be obtained such that an alcohol and a fatty acid are respectively used as starting materials, and ethylene oxides are directly addition-polymerized in the presence of an alkaline or acidic catalyst.

To the contrary, in fatty acid esters of polyoxyalkylene alkyl ethers, even if it is attempted to react an alkylene oxide with a fatty acid alkyl ester (RCOOR') in the presence of an alkaline or acidic catalyst, addition polymerization of the alkylene oxide does not progress. For this reason, after an alcohol is reacted with an alkylene oxide to prepare a polyoxyalkylene alkyl ether, this polyoxyalkylene alkyl ether is reacted with a fatty acid or fatty acid alkyl ester, thereby performing esterification. That is, a two-step reaction is employed.

Alternatively, fatty acid is reacted with alkylene oxide to produce polyoxyalkylene fatty acid ester, and the end of thus produced ester is alkylated to produce fatty acid ester of polyoxyalkylene alkyl ether. In this method, however, much by-products are produced and the content of monoester is about 50%.

The following examples of a one-step reaction between a fatty acid alkyl ester and an alkylene oxide for manufacturing fatty acid esters of polyoxyalkylene alkyl ethers have been reported.

(1) Alkyl acetate is reacted with an alkylene oxide by using a calcinated hydrotalcite compound as a catalyst to synthesize acetic acid ester of polyoxyalkylene alkyl ether (Published Unexamined Japanese Patent Application No. 56-36431).

(2) Using a catalyst consisting of a metal halide of, e.g., zinc or aluminum or consisting of an organometallic compound containing zinc or aluminum, or a combination of such a catalyst and an amine compound, an alkylene oxide is reacted with a carboxylate to manufacture a fatty acid ester of polyoxyalkylene alkyl ether (Published Examined Japanese Patent Application No. 53-24930). For example, using a catalyst consisting of triethyl aluminum or a combination of aluminum chloride and triethyl amine, ethyl acetate is reacted with an ethylene oxide to prepare acetic acid ester of polyoxyethylene ethyl ether.

(3) Ethyl acetate is reacted with an excessive amount of ethylene glycol monoethyl ether in the presence of a strong-acidic cation exchange resin to manufacture acetic acid ester of polyoxyethylene ethyl ether (Published Unexamined Japanese Patent Application No. 54-1038125).

In these methods, however, colored products are obtained and it is difficult to separate the catalyst from the reaction products, thus resulting in unsatisfactory industrial applications.

SUMMARY OF THE INVENTION

It is an object of the present invention to provide a method of easily manufacturing fatty acid ester of polyoxyalkylene alkyl ether by a one-step reaction between a fatty acid alkyl ester and an alkylene oxide.

According to the present invention, there is provided a method of manufacturing a fatty acid ester of polyoxyalkylene alkyl ether, wherein a fatty acid alkyl ester is reacted with an alkylene oxide in the presence of a catalyst consisting of a magnesium oxide added with at least one metal ion selected from the group consisting of $Al^{3+}$, $Ga^{3+}$, $In^{3+}$, $Tl^{3+}$, $Co^{3+}$, $Sc^{3+}$, $La^{3+}$, and $Mn^{2+}$ to manufacture a compound having the following formula:

$$R_1\overset{O}{\overset{\|}{C}}(OR_2)_nOR_3$$

wherein each of $R_1$ and $R_3$ independently represents an alkyl group, and $R_2$ represents an alkylene group and n represents an integer, especially a positive integer.

DETAILED DESCRIPTION OF THE PREFERRED EMBODIMENT

A method of manufacturing fatty acid ester of polyoxyalkylene alkyl ether according to the present invention is characterized by using a catalyst consisting essentially of a magnesium oxide added with at least one metal ion selected from the group consisting of $Al^{3+}$, $Ga^{3+}$, $In^{3+}$, $Tl^{3+}$, $Co^{3+}$, $Sc^{3+}$, $La^{3+}$, and $Mn^{2+}$.

The present inventors found that this catalyst had a special effect in a reaction with an alkylene oxide having active hydrogen to allow the manufacture of a product having a narrow alkylene oxide distribution, and proposed this method in Published Unexamined Japanese Patent Application No. 1-164437.

The present inventors made extensive studies on utility of this catalyst and found that addition polymerization of an alkylene oxide to a fatty acid alkyl ester having no active hydrogen in a molecule could be directly performed using this catalyst.

In a fatty acid alkyl ester ($R_1COOR_3$) used as a starting material according to the present invention, $R_1$ represents alkyl group preferably having 3 to 40 carbon atoms and more preferably 6 to 22 carbon atoms. $R_3$ represents alkyl group preferably having 1 to 30 carbon atoms. Note that the alkyl group in the present invention includes a group having a double bond in a carbon chain (e.g., an alkenyl group).

As an alkylene oxide subjected to addition polymerization with a fatty acid alkyl ester, it is preferred to use one having 2 to 8 carbon atoms. Ethylene oxide, propylene oxide, or butylene oxide having 2 to 4 carbon atoms is more preferable.

Each of the fatty acid alkyl ester and the alkylene oxide, as described above, can be used singly or as a mixture of different types of materials.

The particle size of the magnesium oxide constituting the catalyst used in the method of the present invention is not limited to a specific value, but considering strength of a catalyst, it is preferably falls 1 μm or less.

The content of the metal ion preferably falls within the range of 0.1 to 30 wt % and more preferably 0.5 to 10 wt % of the total weight of the catalyst. The number of types of metal ions is not limited to one, but different types of metal ions may be added to the catalyst.

The catalyst used in the method of the present invention can be manufactured by a method disclosed in Published Unexamined Japanese Patent Application No. 1-164437. However, the following methods of precipitating a metal ion from an aqueous solution containing a metal additive are preferable.

(1) Dipping method: MgO particles are added to and mixed in an aqueous solution containing a metal additive, such as an aqueous aluminum nitrate solution, and are dried and solidified. The solidified product is pulverized and calcinated to prepare catalyst particles.

(2) Coprecipitation method: an aqueous magnesium salt solution such as an aqueous magnesium nitrate solution is mixed with an aqueous solution containing a metal additive ion, such as an aqueous aluminum nitrate solution, and a precipitating agent such as ammonia is added thereto, thereby coprecipitating magnesium and the metal additive as hydroxides in the aqueous solution. These hydroxides are filtered, washed, dried, pulverized, and calcinated to prepare catalyst particles.

(3) Deposition method: an aqueous solution containing a metal additive ion is added to a dispersion in which magnesium oxide particles are dispersed, and a hydroxide of the metal additive is precipitated and deposited on the surface of each magnesium oxide particle. The deposited product is filtered, washed, dried, and calcinated to prepare catalyst particles.

In the above methods, when a catalyst is to be manufactured by a precipitation method such as coprecipitation method or deposition method, unnecessary ions (anions) present in a catalyst slurry can be removed by an ion exchange resin after precipitation, thereby allowing omission of the washing step upon filtering.

The addition polymerization in the method of the present invention can be performed by the normal operational procedures using normal reaction conditions. For example, the reaction temperature preferably falls within the range of 80° to 230° C. and more preferably 120° to 180° C. The reaction pressure preferably falls within the range of 0 to 20 atm and more preferably 2 to 8 atom, although it depends on the reaction temperature.

The content of the catalyst in the method of the present invention depends on the molar ratio of the alkylene oxide to the fatty acid alkyl ester subjected to the reaction. The catalyst content is preferably 0.1 to 20 wt %, and more preferably 0.5 to 10 wt % with respect to the total weight of the fatty acid alkylester.

In the reaction performed by the method of the present invention, a fatty acid alkyl ester and a catalyst are charged in, e.g., an autoclave, and an alkylene oxide is supplied to the autoclave in a nitrogen atmosphere at a predetermined temperature and a predetermined pressure and is reacted with the fatty acid alkyl ester in the presence of the catalyst. After the reaction, the product is cooled, and the catalyst is filtered.

The present invention will be described in detail by way of its examples.

EXAMPLE 1

An aqueous solution obtained by dissolving 30 g of $Al(NO_3)_3.9H_2O$ in 87 g of water was dripped in a dispersion obtained by dispersing 70 g of MgO in 525 ml of water, and the resultant aqueous solution was aged for 30 minutes to obtain a catalyst slurry. After 263 cc of a strong-basic anion exchange resin (tradename: SA-20A available from Mitsubishi Kasei Corp.) pretreated to be an OH type resin were added to the catalyst slurry, the mixture was stirred at room temperature for an hour to perform ion exchange, thereby eliminating $NO_3-$ from the slurry.

After ion exchange was performed, the catalyst slurry was separated from the ion exchange resin by using a screen having a mesh size of 300 μm. After the resultant catalyst slurry was spray-dried, it was calcinated for an hour at 950° C., thereby preparing an Al ion-added MgO catalyst.

22.5 g of the resultant catalyst and 750 g of methyl laurate were charged in the autoclave, and air inside the autoclave was displaced with nitrogen. The mixture was heated to 160° C. under stirring. 772 g of an ethylene oxide were supplied to the autoclave while the atmosphere in the autoclave was maintained at a temperature of 160° C. and a pressure of 3 atm. The ethylene oxide was reacted with the mixture for about an hour in the autoclave, and the reaction solution was cooled to 70° C. The catalyst was then filtered from the reaction solution.

As a result, polyoxyethylene methyl ether laurate having an average ethylene oxide adduct number of 5.0 was obtained.

EXAMPLE 2

24 g of a catalyst obtained following the same procedures as in Example 1 and 804 g of stearyl ester of stearic acid were charged in the autoclave, and a reaction was performed following the same procedures as in Example 1 except that the content of an ethylene oxide was 330 g, thereby obtaining polyoxyethylene stearyl ether stearate having an average ethylene oxide adduct number of 5.0.

EXAMPLE 3

20 g of a magnesium oxide powder were added to 500 g of a 0.9% aqueous gallium nitrate solution and were sufficiently stirred, and subjected to evaporation to dryness.

The product was dried at 110° C. overnight and pulverized. The resultant powder was gradually heated in a nitrogen flow and was kept heated at 600° C. for 2 hours, thereby obtaining a MgO catalyst added with Ga ions.

25 g of the resultant catalyst and 750 g of methyl laurate were charged in the autoclave, and air in the autoclave was displaced with nitrogen. The mixture was heated to 180° C. under stirring. 1,390 g of an ethylene oxide were supplied to the autoclave while it was maintained at a temperature of 180° C. and a pressure of 3 atm. The mixture was reacted for about an hour, the reacted solution was cooled to 70° C., and the catalyst was filtered.

As a result, polyoxyethylene methyl ether laurate having an average ethylene oxide adduct number of 9.0 was obtained.

EXAMPLES 4–9

MgO catalysts respectively added with metal ions, i.e., $In^{3+}$, $Tl^{3+}$, $Co^{3+}$, $Sc^{3+}$, $La^{3+}$, and $Mn^{2+}$ shown in the following table were manufactured, and fatty acid esters of polyoxyalkylene alkyl ethers were manufactured using these MgO catalysts, following the same procedures as in Example 1 or 3. The types of the resultant fatty acid esters of polyoxyalkylene alkyl ethers and their average oxyalkylene adduct numbers are as follows.

TABLE

| Example | metal ion | product | oxyalkylene addition molar number | procedure |
|---|---|---|---|---|
| 4 | $In^{3+}$ | A | 3.0 | Example 1 |
| 5 | $Tl^{3+}$ | B | 3.0 | Example 1 |
| 6 | $Co^{3+}$ | C | 3.0 | Example 1 |
| 7 | $Sc^{3+}$ | C | 3.0 | Example 3 |
| 8 | $La^{3+}$ | B | 7.0 | Example 3 |
| 9 | $Mn^{2+}$ | A | 7.0 | Example 1 |

[1]A: polyoxyethylene methyl ether laurate
B: polyoxyethylene stearyl ether stearate
C: polyoxyethylene methyl ether stearate
[2]average alkylene oxide adduct number As is apparent from the above table, various fatty acid esters of polyoxyalkylene alkyl ethers can be manufactured using the magnesium oxide catalysts respectively added with $In^{3+}$, $Tl^{3+}$, $Co^{3+}$, $Sc^{3+}$, $La^{3+}$, and $Mn^{2+}$.

As has been described above, according to the method of the present invention, direct addition polymerization of an alkylene oxide with a fatty acid alkyl ester can be performed using a magnesium oxide catalyst added with each of various types of metal ions. According to the present invention, fatty acid esters of polyoxyalkylene alkyl ethers can be easily manufactured by a one-step reaction from a fatty acid alkyl ester relatively easily accessible as an industrial material.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method of manufacturing fatty acid esters of polyoxyalkylene alkyl ethers, wherein fatty acid alkyl ester having the formula:

$$R_1-\overset{\overset{O}{\|}}{C}-O-R_3$$

wherein $R_1$ represents an alkyl group having 3 to 40 carbon atoms and $R_3$ represents an alkyl group having 1 to 30 carbon atoms is reacted with alkylene oxide in the presence of a catalyst consisting essentially of magnesium oxide and 0.1% to 10% based upon the weight of the catalyst of at least one metal ion selected from the group consisting of $Al^{3+}$, $Ga^{3+}$, $In^{3+}$, $Tl^{3+}$, $Co^{3+}$, $Sc^{3+}$, $La^{3+}$, and $Mn^{2+}$ to manufacture a compound having the following formula:

$$R_1\overset{\overset{O}{\|}}{C}(OR_2)_nOR_3$$

wherein $R_1$ and $R_3$ are as defined above, $R_2$ represents an alkylene group, and n is an integer.

2. A method according to claim 1, wherein the metal ion is $Al^{3+}$ or $Ga^{3+}$.

3. A method according to claim 1, wherein a content of the metal ion falls within a range of 0.5 to 10 wt % of a total weight of the catalyst.

4. A method according to claim 1, wherein the alkylene oxide has 2 to 8 carbon atoms.

5. A method according to claim 1, wherein the alkylene oxide is at least one oxide selected from the group consisting of ethylene oxide, propylene oxide, and butylene oxide.

6. A method according to claim 1, wherein a reaction temperature falls within a range of 80° to 230° C.

7. A method according to claim 1, wherein a reaction temperature falls within a range of 120° to 180° C.

8. A method according to claim 1, wherein a reaction pressure falls within a range of 0 to 20 atm.

9. A method according to claim 1, wherein a reaction pressure falls within a range of 2 to 8 atm.

10. A method according to claim 1, wherein an amount of the catalyst falls within a range of 0.1 to 20 wt % of a total weight of the fatty acid alkyl ester.

11. A method according to claim 1, wherein an amount of the catalyst falls within a range of 0.5 to 10 wt % of a total weight of the fatty acid alkyl ester.

12. The method of claim 1 wherein n is a positive integer.

* * * * *